US008490463B2

United States Patent
Yost et al.

(10) Patent No.: US 8,490,463 B2
(45) Date of Patent: Jul. 23, 2013

(54) ASSESSMENT AND CALIBRATION OF A CRIMP TOOL EQUIPPED WITH ULTRASONIC ANALYSIS FEATURES

(75) Inventors: William T. Yost, Newport News, VA (US); Daniel F. Perey, Yorktown, VA (US); K. Elliott Cramer, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 403 days.

(21) Appl. No.: 12/881,431

(22) Filed: Sep. 14, 2010

(65) Prior Publication Data

US 2012/0060585 A1    Mar. 15, 2012

(51) Int. Cl.
*G01N 29/04* (2006.01)

(52) U.S. Cl.
USPC .................. 73/1.82; 73/600; 73/602; 73/609; 73/610

(58) Field of Classification Search
USPC .................. 73/1.82, 600, 602, 609, 610, 613
See application file for complete search history.

(56) References Cited

U.S. PATENT DOCUMENTS

| | | | |
|---|---|---|---|
| 6,810,743 B2 * | 11/2004 | Madaras et al. | 73/598 |
| 7,181,942 B2 * | 2/2007 | Yost et al. | 72/17.2 |

* cited by examiner

*Primary Examiner* — Hezron E Williams
*Assistant Examiner* — Paul West
(74) *Attorney, Agent, or Firm* — Andrea Z. Warmbier; Helen M. Galus

(57) ABSTRACT

A method is provided for calibrating ultrasonic signals passed through a crimp formed with respect to a deformable body via an ultrasonically-equipped crimp tool (UECT). The UECT verifies a crimp quality using the ultrasonic signals. The method includes forming the crimp, transmitting a first signal, e.g., a pulse, to a first transducer of the UECT, and converting the first signal, using the first transducer, into a second signal which defines an ultrasonic pulse. This pulse is transmitted through the UECT into the crimp. A second transducer converts the second signal into a third signal, which may be further conditioned, and the ultrasonic signals are calibrated using the third signal or its conditioned variant. An apparatus for calibrating the ultrasonic signals includes a pulse module (PM) electrically connected to the first and second transducers, and an oscilloscope or display electrically connected to the PM for analyzing an electrical output signal therefrom.

16 Claims, 4 Drawing Sheets

ASSESSMENT AND CALIBRATION OF A CRIMP TOOL EQUIPPED WITH ULTRASONIC ANALYSIS FEATURES

ORIGIN OF THE INVENTION

The invention described herein was made by employees of the United States Government and may be manufactured and used by or for the Government for governmental purposes without payment of any royalties thereon or therefor.

TECHNICAL FIELD

The present invention relates to a method and an apparatus for calibrating a crimping tool having transducers adapted for determining, via ultrasonic signal generation and processing, the quality of a resultant crimped joint.

BACKGROUND OF THE INVENTION

Crimping is a cold-working process used to join mutually-deformable objects, at least one of which is typically constructed of metal or another malleable material. For example, in forming a crimped electrical connection, a wire may be deformed with respect to a barrel or a ferrule in order to form a crimped joint, hereinafter referred to as a crimp for simplicity. Crimping tools are the devices most typically used to compress a bundle of wires together, and to compress the ferrule tightly around the bundled wires. An improperly crimped ferrule/wire connection may contain loose wires, and the deformation of the ferrule may provide an inadequate clamping force.

Conventional testing of a pull-out force of a crimp is performed manually. That is, the crimp, along with any settings of the particular tool used to form the crimp, are evaluated via the pull force required to separate the crimped ferrule from the wire or bundled wires therein. Once the crimps are determined to support a threshold minimum load, usually set on the basis of wire gauge and crimp ferrule qualities, the crimping tool is placed in service. However, conventional pull testing may inadequately measure transport across the crimps, and therefore such pull test results are not closely linked with electrical conduction properties of the resultant crimp. Therefore, calibration of conventional crimping tools based primarily on pull testing results may be less than optimal.

SUMMARY OF THE INVENTION

Accordingly, a method and an apparatus are provided herein for calibrating an ultrasonically-equipped crimp tool (UECT) of the type set forth in U.S. Pat. No. 7,181,942 to Yost et al., the contents of which are hereby incorporated by reference in their entirety. The UECT as disclosed in Yost et al. and herein provides in-situ crimp tool evaluation possibilities, whether conducted alone or in conjunction with pull testing, e.g., pre-operational ultrasonic verification and measurement of the UECT. As the UECT is repeatedly used, physical wear and use may affect alignment, causing the UECT to gradually fall out of tolerance.

The present invention therefore provides for the independent verification of the proper alignment of jaw and anvil portions of the UECT, as well as proper functioning of an ultrasonic pathway of the UECT and its related circuitry. Once properly calibrated, the UECT may be used to form crimps with the assurance that all elements in the crimping process are set for optimal performance, e.g., the supporting electronics of any system using the UECT are all working properly, the jaws of the UECT are properly aligned, etc.

In particular, a method is provided for calibrating an ultrasonic signal that is passed through the region of a crimp formed with respect to a deformable body using the UECT. The method includes forming the crimp using the UECT, including processing the ultrasonic signal to determine a number of points of contact between the deformable body and the UECT. The method further includes transmitting a first signal, e.g., a pulse signal, via a pulse module (PM) to a first transducer, and then converting the first signal, using the first transducer, into a second signal. The second signal defines an ultrasonic pulse. The second signal then passes through the UECT and into the crimp. Additionally, the method includes converting the second signal into a third signal using a second transducer, transmitting the third signal to the PM, and then calibrating the ultrasonic signal using the third signal. A display, whether stand alone or part of an oscilloscope, may be used with the PM to display and analyze the third signal or a conditioned variant thereof, with an optional host machine used to record calibration results and/or to facilitate analysis.

The method may include automatically conditioning the third signal using at least one of damping, high-pass filtering, low-pass filtering, and signal attenuation. The first signal may be configured as a short-rise time pulse or other suitable pulse signal. The second signal may have a single frequency adapted for suppressing a predetermined set of interference effects, or it may be a spectrum of different frequencies. In one embodiment, calibrating the ultrasonic signal includes comparing a first waveform, i.e., the third signal or its conditioned variant, generated using a calibrated crimp plug with a second waveform generated using an actual crimp to thereby determine a variance between the two waveforms. The variance is compared to a calibrated threshold, and calibrating the ultrasonic signal may be achieved via the results of this comparison.

An apparatus for calibrating an ultrasonic signal that is passed through the crimp region includes the PM, which is electrically connected to each of the first and second transducers, the first transducer being in communication with the second transducer through the crimp. The PM generates and transmits a first pulse signal to the first transducer. The apparatus also includes an oscilloscope electrically connected to the PM, which may be used to identify and analyze an electrical output signal, i.e., the third signal or a conditioned variant thereof as noted elsewhere above, from the PM. The first transducer converts the first pulse signal from the PM into an ultrasonic pulse signal, and transmits the ultrasonic pulse signal through the crimp to the second transducer. The second transducer generates an electrical signal, and transmits the electrical signal to the PM for use in generating the electrical output signal. A calibration action may be performed using the electrical output signal, e.g., via a display, an oscilloscope, and/or a host machine connected thereto.

The above features and advantages and other features and advantages of the present invention are readily apparent from the following detailed description of the best modes for carrying out the invention when taken in connection with the accompanying drawings.

DESCRIPTION OF THE PREFERRED EMBODIMENTS

Figure 1:
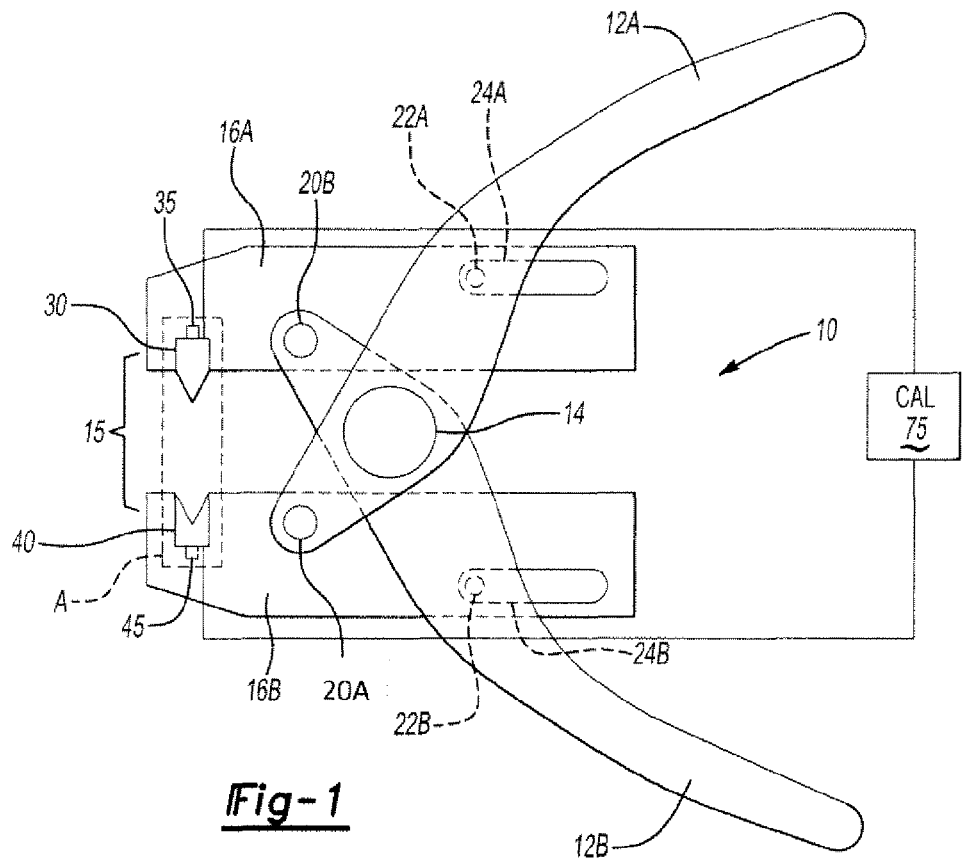
FIG. 1 is a schematic side view illustration of an ultrasonically-equipped crimp tool (UECT) in an uncompressed position, and a calibration system adapted for calibrating the UECT.
Figure 2:
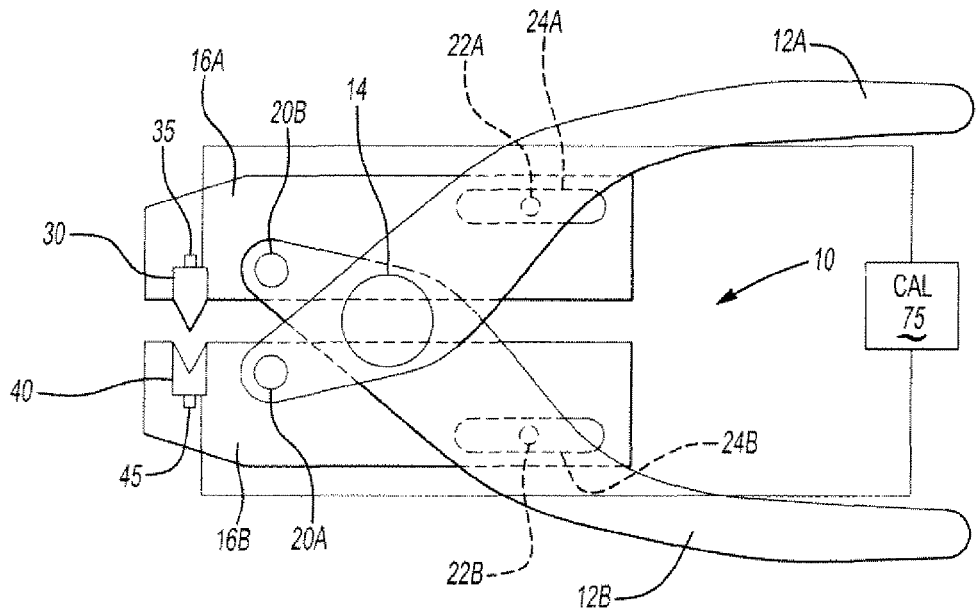
FIG. 2 is a schematic side view illustration of the UECT and calibration system of FIG. 1, with the UECT in a compressed position.

Referring to the drawings wherein like reference numbers represent like components throughout the several figures, FIGS. 1 and 2 show an ultrasonically-equipped crimp tool or UECT 10 in an open or uncompressed state (FIG. 1) and a closed or compressed state (FIG. 2). A calibration system (CAL) 75 is electrically connected to the UECT 10, and is adapted for calibrating the UECT and an ultrasonic signal passed through a region of a crimp formed with respect to a deformable body, as explained below with reference to FIGS. 4-6.

The shown UECT 10 includes a pair of handles 12A and 12B which are each connected to, and allowed to rotate about, a coaxial pivot 14. The UECT 10 also includes jaws 16A and 16B, which are positioned opposite one another. Handle 12A is pivotally attached to the jaw 16B at a pivot 20A, and handle 12B is likewise pivotally attached to jaw 16A at a pivot 20B. Guide pins 22A and 22B are secured on the handles 12A and 12B, respectively. Jaws 16A and 16B are respectively provided with elongated slots 24A and 24B, which extend longitudinally therealong, and are sufficiently disposed to engage a respective one of the guide pins 22A and 22B.

Closure of the handles 12A and 12B, best shown in FIG. 2, causes the handles to rotate about the coaxial pivot 14, and affects a closure of the jaws 16A and 16B. The pivot mounting of the jaws 16A, 16B on the handles 12A, 12B and cooperation of guide pins 22A, 22B with respective slots 24A and 24B causes the jaws 16A, 16B to maintain orientation with respect to one another.

Referring to FIGS. 1 and 2 together, the UECT 10 includes compressing means 15 having a punch 30 and an anvil 40. The punch 30 and anvil 40, configured and oriented as shown, is just one possible embodiment of the compressing means 15. Those of ordinary skill in the art will recognize other structures providing a suitable compressive function within the scope of the present invention. As shown in the area generally demarcated by dotted line A, the UECT 10 includes a transmitting transducer 35 and a receiving transducer 45, whether configured separately or as a single device.

Figure 3:
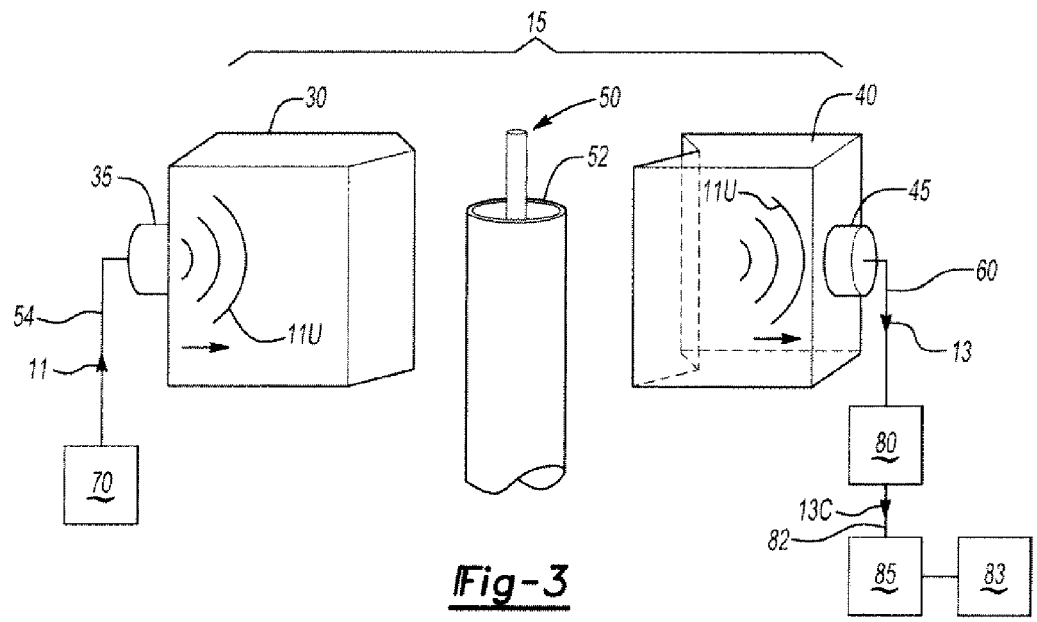
FIG. 3 is an isolated and simplified schematic perspective view of an area outlined in FIG. 1, showing an arrangement of the ultrasonic components and related circuitry of the UECT of FIG. 1 according to one embodiment.

Referring to FIG. 3, the calibration system 75 of FIGS. 1 and 2 may include a pulse module (PM) 70, i.e., a pulse-generating and pulse-receiving device having the functionality set forth below, an oscilloscope 81 (shown in FIG. 4) having a display 85, and a host machine 83. In another embodiment the display 85 may be a separate or a stand-alone device. The compressing means 15 of UECT 10, also shown in FIGS. 1 and 2, engages the wire(s) 50 and a ferrule 52. For simplicity, wire 50 is shown as a single wire strand, although multiple strands of wires may be bundled as a cable without departing from the intended scope of the invention. As the punch 30 and anvil 40 are brought together (see FIG. 2) they at least partially deform the ferrule 52 with respect to the wire 50, forming a crimp suitable as a mechanical and/or an electrical connection.

Once the punch 30 and anvil 40 begin compressing the ferrule 52, a first signal 11, e.g., a voltage spike having a calibrated peak value, is sent from PM 70 through an electrical connection 54 to the transmitting transducer 35. The first signal 11 activates the transmitting transducer 35, which is ultrasonically-coupled to a non-operative surface of the punch 30. Transducer 35 transforms the first signal 11 into a second signal 11U, which in one embodiment is an acoustic pulse signal having a calibrated single frequency falling within the ultrasonic frequency range. For example, this range may be defined as approximately 20 KHz to approximately 300 KHz, more generally understood as the range of frequencies above the human audible frequency range. In another embodiment the second signal 11U may be a range or spectrum of different frequencies.

The second signal 11U then travels through the punch 30 and ferrule 52, through any contacts made by the compression between the ferrule and wire 50, through the wire, the opposing side of the ferrule, the anvil 40, and, ultimately, to the receiving transducer 45. Transducer 45 may be ultrasonically-coupled to a non-operative face of the anvil 40. The method of sending an acoustic signal such as signal 11U from one side of the apparatus and receiving it at the opposing side is called a "pitch-catch" technique, as understood in the art.

The receiving transducer 45 transforms the second signal 11U as it is received in the anvil 40 into a third signal 13. Third signal 13 may be sent via an electrical connection 60 to receiver circuitry 80 suitable for processing and conditioning of the third signal, e.g., amplification, high-pass filtering, low-pass filtering, and attenuation. A conditioned electrical signal 13C is the output of the receiver circuitry 80, and it may be sent via electrical connection 82 to a display 85, e.g., a display portion of the oscilloscope 81 shown in FIG. 4. Calibration data and data recording may be provided via the host machine 83.

Still referring to FIG. 3, as the applied pressure via UECT 10 of FIGS. 1 and 2 deforms the ferrule 52 with respect to the wire(s) 50, a number of points of contact or asperities result between the wires) and the ferrule. These asperities enable increased ultrasonic transmission from the transmitting transducer 35 to the receiving transducer 45. The number of pathways for ultrasonic transmission through the ferrule 52 and wire(s) 50 correspond to the number of pathways for electrical conduction. Deformation of the ferrule 52 produces a crimp connection between the ferrule and the wire(s).

One way of determining the desirability of the resultant crimp connection, i.e., the mechanical strength and the amount of electrical transmission between the wire and the connector, is for the user to first make a series of test crimp connections using wire and crimp connectors. The user may record the output associated with each test crimp connection. The test crimp connections may be submitted to ultrasonic testing and, if desired, to mechanical destructive pull testing in order to determine their electrical and mechanical characteristics. This technique thereby allows the user to assess the desirability of the crimp connection while it is being made. The comparison to be performed between the desired value and measured value during use of the UECT 10 may be performed by the operator, or it may be automatically accomplished using oscilloscope 81 and host machine 83.

Figure 4:
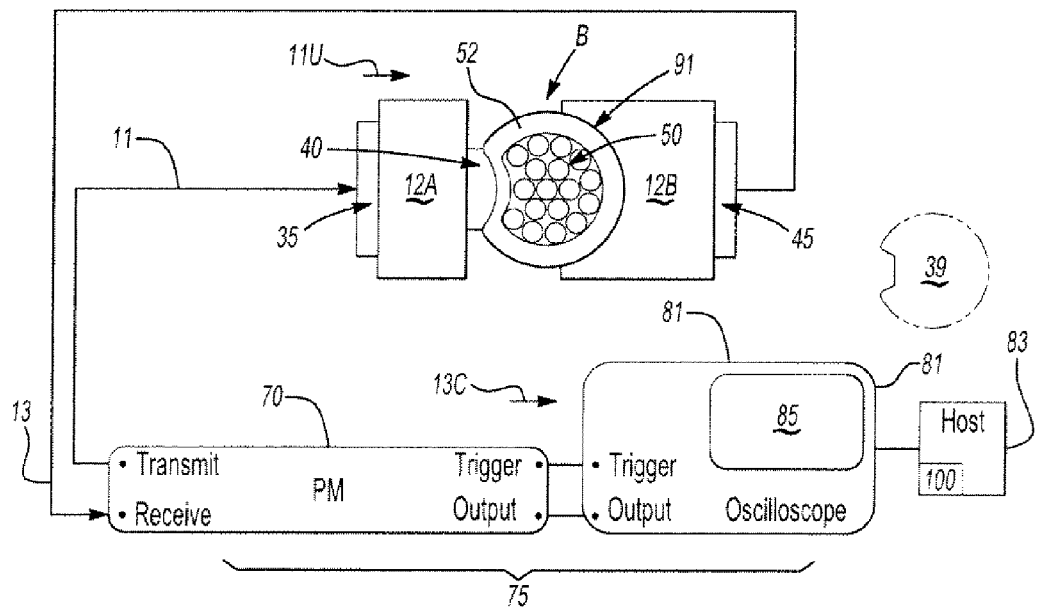
FIG. 4 is a schematic illustration of component parts used in a calibration of the UECT shown in FIG. 1.

Referring to FIG. 4, the UECT 10 is electrically connected to the calibration system 75. The calibration system 75 includes the PM 70 and oscilloscope 81, and may include host machine 83 adapted for executing an algorithm 100 as set forth below with reference to FIG. 4A. Host machine 83 may include multiple digital computers or data processing devices each having one or more microprocessors or central processing units (CPU), read only memory (ROM), random access memory (RAM), electrically-erasable programmable read only memory (EEPROM), a high-speed clock, analog-to-digital (A/D) circuitry, digital-to-analog (D/A) circuitry, and any required input/output (I/O) circuitry and devices, as well as signal conditioning and buffer electronics. Individual control algorithms resident in the host machine 83, or readily accessible thereby, may be stored in ROM and automatically executed to provide the desired calibration functionality.

The present invention calibrates ultrasonic signals, i.e., signal 11U, passed through the crimp during ultrasonic verification of the crimp. This action may be a verification that the ultrasonic signals passing through the crimp and the UECT 10 are working properly, i.e., there is a good alignment of the transducers 35, 45 with the jaws 12A, 12B, and that all signal levels are within a calibrated tolerance.

Figure 4A:
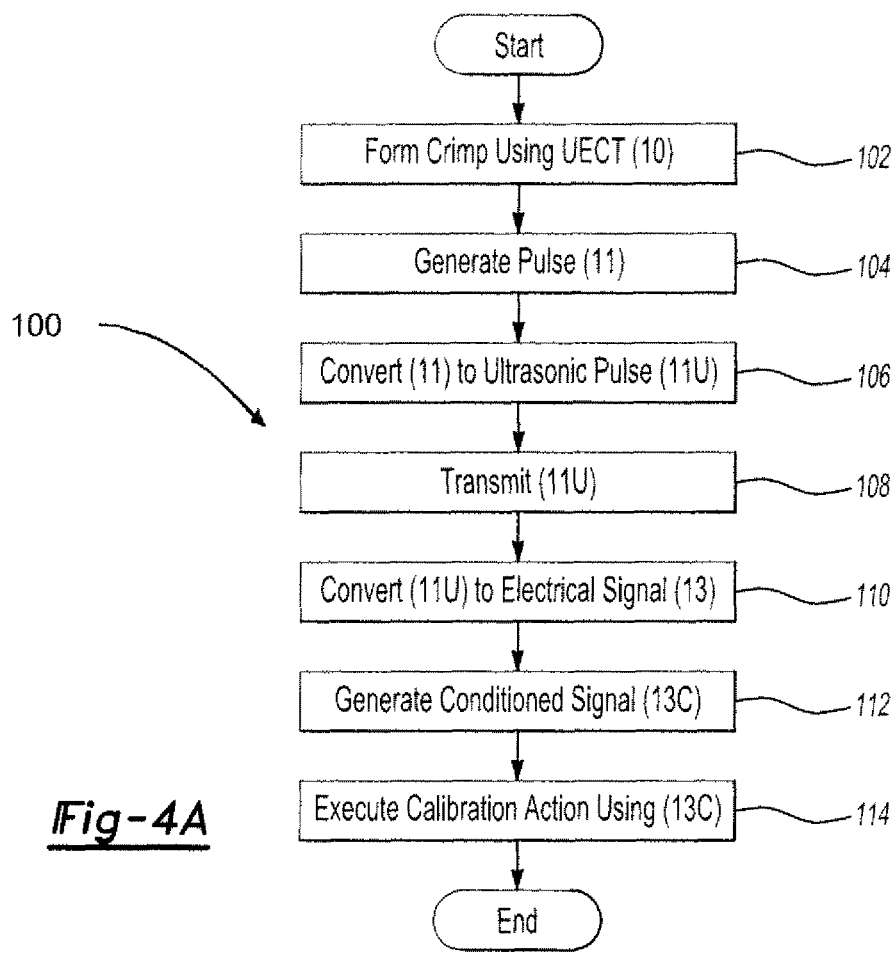
FIG. 4A is a flow chart describing a method for calibrating the UECT shown in FIG. 1.

Referring to FIG. 4 in conjunction with the algorithm 100 set forth in FIG. 4A, after a crimp is formed at step 102 using the UECT 10 shown in FIGS. 1-3 as described above, or using a crimping tool of similar design, first signal 11, e.g., an electrical short-rise time pulse or voltage spike, is generated at step 104 by the PM 70. The first signal 11 is then transmitted by the PM 70 to the transmit transducer 35.

At step 106, using the transmit transducer 35, the first signal 11 is converted into the second signal 11U, e.g., an ultrasonic pulse. The transducer 35 may be configured as a low-Q compression unit, such as damped or of special design, although shear transducers may also be used, as will be understood by those of ordinary skill in the art. The second signal 11U may have a controlled or a single-frequency to facilitate suppression of any frequency interference effects that may otherwise skew the analysis. In another embodiment, multiple frequencies may be used, or a "chirp" signal that contains a spectrum of frequencies, with the frequency content of the received waveform used to perform the desired calibration as set forth below.

At step 108, the second signal 11U passes through jaw 12A, to the anvil 40, and into the crimp region, indicated generally by arrow B, as the jaws 12A, 12B compress the ferrule 52 around the wire(s) 50. Depending on the required crimp level, and ultimately depending on the crimp quality, the second signal 11U passes through the crimped ferrule 52 and wire(s) 50, through the resultant conforming wedge 91 of the crimp, and into the jaw 12B.

At step 110, the second signal 11U impinges on the receive transducer 45, where it is directly converted into a third signal 13, e.g., a generally sinusoidal waveform, and passed through the PM 70.

At step 112, in the PM 70, the third signal 13 may undergo signal conditioning steps, e.g., damping, amplification, high-pass filtering, low-pass filtering, attenuation, etc., and the resultant conditioned signal 13C passed to the display 85, e.g., a display portion of oscilloscope 81 or a stand-alone display.

At step 114, using signal 13 and/or 13C, a calibration action may be executed for the mechanical and/or electrical settings of the UECT 10 shown in FIGS. 1-3. Once calibrated, the UECT 10 may be used to form crimps with an assurance that all elements in the process are set for optimum performance.

Figure 5:
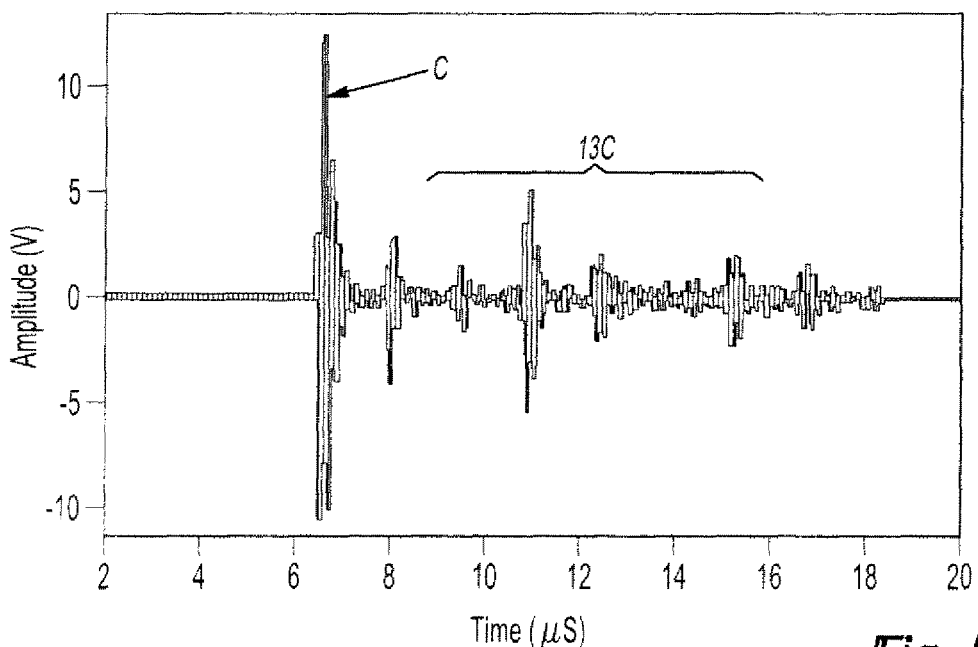
FIG. 5 is a schematic waveform for a signal usable with the calibration method of FIG. 4A.

Referring to FIG. 5, the host machine 83 of FIG. 4 may be used in conjunction with the oscilloscope 81 for signal identification and analysis, data collection, etc. Oscilloscope 81 may display the conditioned signal 13C to a user via display 85, which may be recorded via host machine 83 if so desired. An objectively "good" or passing crimp may be shown to satisfy certain ultrasonic energy levels on any first-received signal, indicated in FIG. 5 by arrow C, and corresponding to the third signal 13 or the conditioned variant 13C of the third signal, depending on the embodiment.

Referring again to FIG. 4, a calibration plug 39 is shown in phantom. Plug 39 may be substituted for the ferrule 52 and wire(s) 50 of an actual crimp to facilitate calibration, i.e., the plug may be used as a calibrated standard. The calibration procedure set forth above remains the same, with the plug 39 placed at an appropriate position within the UECT 10 of FIGS. 1 and 2. As the UECT 10 is activated, e.g., by squeezing the handles 12A, 12B, a time record or trace displayed on the oscilloscope 81 shows the transmitted signal through the plug 39, i.e., third signal 13 or the conditioned third signal 13C. Hence, the host machine 83, or a user viewing the oscilloscope 81, may verify whether all components are working properly, and that all signals are expected and appropriate and/or consistent.

Using the plug 39 as shown in phantom in FIG. 4, one may verify that the electronics are functioning properly, the transducers 35, 45 are both in good contact and alignment with respect to the other structure of the UECT 10, and the jaws 16A, 16B remain in proper alignment during the crimping process. This method also ensures that an adequate amount of ultrasonic energy is passed through the crimping region (arrow B of FIG. 4), with this energy remaining within a calibrated tolerance.

Figure 6:
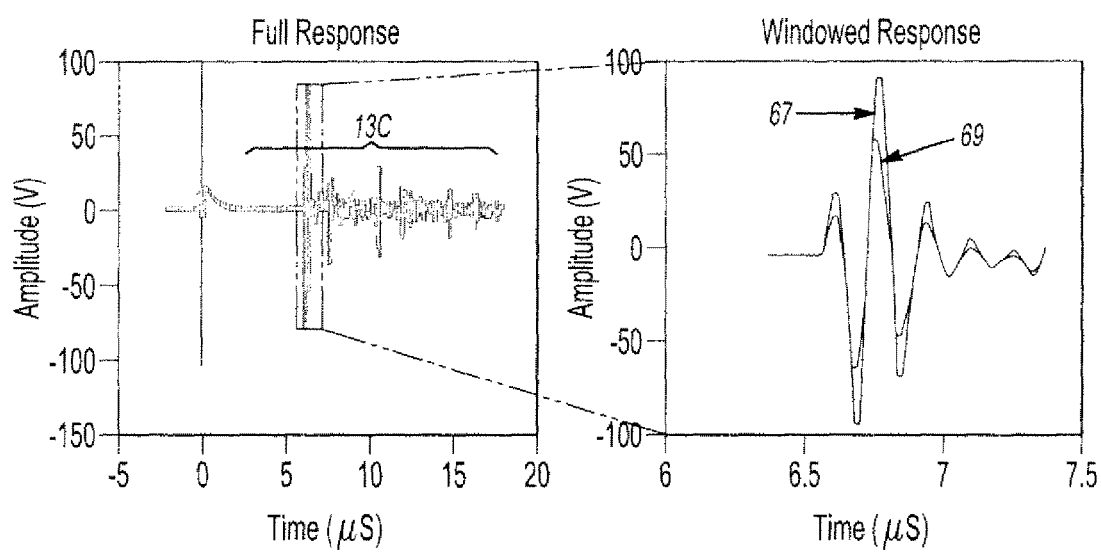
FIG. 6 is a schematic waveform comparison that may be used in the calibration of the UECT shown in FIGS. 1 and 2.

Referring to FIG. 6, the calibration step 114 of FIG. 4A may be executed via a comparison of waveforms of respective third signal 13 and/or conditioned third signal 13C. That is, given a full response displayed via oscilloscope 81 of FIG. 4, one may check a first/actual waveform 67 of a signal 13, 13C from an actual crimp to a second/calibrated waveform 69 of a signal 13, 13C determined using the plug 39. Depending on the material chosen for the plug 39, the waveform through the plug, i.e., waveform 69, bears some definable relationship to the waveform 67 through the actual or "good" crimp. This relationship may be compared to a calibrated minimum and/or maximum tolerance, a range of tolerances, or another calibrated threshold value. The method and apparatus set forth above therefore makes it possible to confirm a number of critical conditions that must be fulfilled for correct crimping operation and waveform interpretation.

While the best modes for carrying out the invention have been described in detail, those familiar with the art to which this invention relates will recognize various alternative designs and embodiments for practicing the invention within the scope of the appended claims.

What is claimed as new and desired to be secured by Letters Patent of the United States is:

1. A method of calibrating an ultrasonically-equipped crimp tool (UECT) used to form a crimp with respect to a deformable body, the method comprising:
   forming the crimp using the UECT;
   generating and transmitting a first signal, using a pulse module (PM), to a first transducer of the UECT;
   converting the first signal, using the first transducer, into a second signal, wherein the second signal defines an ultrasonic pulse having at least one calibrated frequency;
   transmitting the second signal through the UECT and into the crimp;

positioning a calibration plug with respect to the UECT in place of the crimp;

transmitting the second signal through the UECT and into the calibration plug;

converting the second signal, using a second transducer of the UECT, into a third signal for each of the crimp and the calibration plug;

displaying the third signals; and calibrating the UECT using the third signals, including determining a variance between the third signals;

comparing the variance to a calibrated threshold; and executing a calibration action for a mechanical and/or an electrical setting of the UECT when the variance exceeds the calibrated threshold.

2. The method of claim 1, wherein calibrating the UECT includes transmitting the third signals to the PM, and wherein displaying the third signals includes displaying the third signals using an oscilloscope.

3. The method of claim 1, further comprising: automatically conditioning the third signals using at least one of amplification, damping, high-pass filtering, low-pass filtering, and attenuation.

4. The method of claim 1, wherein transmitting a first signal includes transmitting one of a voltage spike and a short-rise time pulse signal.

5. The method of claim 1, wherein the at least one calibrated frequency is one of: a spectrum of different frequencies and a single frequency adapted for suppressing a predetermined set of interference effects.

6. The method, of claim 1, wherein transmitting the second signal through the UECT and into the crimp region includes transmitting the second signal through each of the crimp and a jaw portion of the UECT.

7. A method of calibrating an ultrasonically-equipped crimp tool (UECT) that forms a crimp with respect to a deformable ferrule, the method comprising;

forming the crimp between the ferrule and at least one wire using the UECT, including processing the ultrasonic signal to thereby determine a number of points of contact between the deformable ferrule and the UECT;

generating and transmitting a short-rise time pulse signal, using a pulse module (PM), to a first transducer of the UECT;

converting the short-rise time pulse signal, using the first transducer, into an ultrasonic pulse signal;

transmitting the ultrasonic pulse signal through the UECT and into the crimp;

positioning a calibration plug with respect to the UECT in place of the crimp;

transmitting the ultrasonic pulse signal through the UECT and into the calibration plug;

converting the ultrasonic pulse signals, using a second transducer of the UECT, into corresponding electrical signal;

displaying the electrical signals;

determining a variance between the corresponding electrical signals;

comparing the variance to a calibrated threshold; and executing a calibration action for as mechanical and/or electrical setting of the UECT when the variance exceeds the calibrated threshold.

8. The method of claim 7, further comprising: automatically conditioning the corresponding electrical signals using at least one of amplification, damping, high-pass filtering, low-pass filtering, and attenuation.

9. The method of claim 7, wherein calibrating the UECT includes transmitting the electrical signals to the PM, and wherein displaying the corresponding electrical signals includes displaying the electrical signals using an oscilloscope.

10. The method of claim 7, wherein the ultrasonic pulse signal is one of: a spectrum of different frequencies and as single frequency adapted for suppressing a predetermined set of interference effects.

11. The method of claim 7, wherein transmitting the ultrasonic pulse signal through the UECT and into the crimp includes transmitting the second pulse through each of the crimp and a jaw portion of the UECT.

12. An apparatus for calibrating an ultrasonically-equipped crimp tool (UECT) that forms a crimp with respect to a deformable body, the apparatus comprising:

a pulse module (PM) that is electrically connected to each of a first transducer and a second transducer of the UECT, the first transducer being in communication with the second transducer through the crimp, wherein the PM is adapted for generating and transmitting a first pulse signal to the first transducer;

a display electrically connected to the PM, and adapted for displaying an electrical output signal from the PM to facilitate analysis of the electrical output signal; and a calibration plug;

wherein the first transducer is configured to convert the first pulse signal from the PM into an ultrasonic pulse signal, and to separately transmit the ultrasonic pulse signal through the crimp and the calibration plug to the second transducer, and wherein the second transducer is adapted for generating a corresponding electrical signal for each of the calibration plug and the crimp, and for transmitting the corresponding electrical signals to the PM for use in displaying a variance between the corresponding electrical signals to thereby execute a calibration action for a mechanical and/or electrical setting of the UECT.

13. The apparatus of claim 12, including an oscilloscope, wherein the display is a display portion of the oscilloscope.

14. The apparatus of claim 12, wherein the PM is adapted for processing the electrical signals to generate the electrical output signal by conditioning the electrical signal using at least one of: amplification, damping, high-pass filtering, low-pass filtering, and attenuation.

15. The apparatus of claim 12, wherein the PM is adapted for generating the first pulse signal as one of a short-rise time pulse and a voltage spike.

16. The apparatus of claim 12, further comprising a host machine in communication with the display, wherein the host machine is adapted for recording the electrical signals and the variance to facilitate calibration of the UECT.

* * * * *